(12) United States Patent
Ferrell, Jr. et al.

(10) Patent No.: US 7,338,673 B2
(45) Date of Patent: Mar. 4, 2008

(54) MEDICATED PATCH FOR TREATING BEE AND WASP STINGS

(76) Inventors: Thomas H. Ferrell, Jr., 184 Chestnut Land Rd., New Milford, CT (US) 06776; Stephen A. Russell, 12237 Doncaster Rd., Knoxville, TN (US) 37932

( * ) Notice: Subject to any disclaimer, the term of this patent is extended or adjusted under 35 U.S.C. 154(b) by 365 days.

(21) Appl. No.: 11/121,843

(22) Filed: May 5, 2005

(65) Prior Publication Data

US 2006/0057189 A1    Mar. 16, 2006

(51) Int. Cl.
*A61K 65/00* (2006.01)
*A61F 13/00* (2006.01)

(52) U.S. Cl. .................. 424/751; 424/449; 514/830

(58) Field of Classification Search ............ 424/449, 424/751; 514/830
See application file for complete search history.

(56) References Cited

U.S. PATENT DOCUMENTS

| | | |
|---|---|---|
| 2,335,015 A * | 11/1943 | Lantheaume |
| 4,557,934 A | 12/1985 | Cooper |
| RE34,692 E | 8/1994 | Becher |
| 5,736,153 A | 4/1998 | Lamers |
| D415,836 S | 10/1999 | Dunshee et al. |
| 6,353,145 B1 * | 3/2002 | Church |
| RE37,934 E | 12/2002 | Hoffmann |
| 6,528,086 B2 | 3/2003 | Zhang |
| 2002/0004063 A1 | 1/2002 | Zhang |
| 2002/0068891 A1 * | 6/2002 | Weathers |

* cited by examiner

*Primary Examiner*—Michele Flood
(74) *Attorney, Agent, or Firm*—Alix, Yale & Ristas, LLP

(57) ABSTRACT

A medicated patch for extracting bee/wasp sting toxins from the human skin includes a flexible substrate layer that has a planar adhesive surface and an annular shape. An annular receptacle is centrally registered on the adhesive surface and is permanently affixed to the substrate layer. A poultice is nested on the receptacle and protrudes upwardly and away from the substrate layer such that the poultice becomes effectively intercalated between the human body surface and the substrate layer when a user affixes the medicated patch onto the human body surface. The poultice is housed in an inactive and dry state during pre-application conditions and is adaptable to an active and hydrated state during application procedures such that the poultice can effectively extract toxins from the human body surface.

15 Claims, 1 Drawing Sheet

MEDICATED PATCH FOR TREATING BEE AND WASP STINGS

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to medicated patches and, more particularly, to a medicated patch for treating bee and wasp stings.

2. Prior Art

Because of the ease of access, dynamics of application, large surface area, vast exposure to the circulatory and lymphatic networks, and non-invasive nature of the treatment, the delivery of pharmaceutically-active agents through the skin has long been a promising concept. This is true whether the bioavailability desired is systemic, dermal, regional or local.

Many medical formulations topically applied onto human body surfaces are in the form of pastes, gels, ointments, cream, and solutions less than solid states that are vulnerable to being wiped off inadvertently or flowing away from the application site. For example, after a solution formulation is applied onto human skin, it can flow away quickly and thus, result in a short contact time with the original application site. After a cream is applied onto the skin of an arm, it can be rubbed off in the daily activities, if not protected by a cover. It would be advantageous to have a means of covering the medication after it is applied.

The advantages of topical delivery include, but are not limited to: avoidance of the risks associated with parenteral treatment; elimination of the inconveniences of parenteral treatment; avoidance of the variable rates of absorption and metabolism inherent in oral treatment; increasing the continuity of drug administration by permitting delivery of agents with short biological half-lives; and elimination of gastrointestinal irritation resulting from exposing the gastrointestinal tract to pharmaceutical actives, preservatives, tableting agents, and the like. Most importantly, topical delivery possesses the potential for effectively treating conditions which are local in nature (or which exhibit local manifestations), systemically as well as locally with the same treatment regimen. This is especially true for incidents of bee or wasp stings.

Accordingly, a need remains for a medicated patch for treating bee and wasp stings in order to overcome the above-noted shortcomings. The present invention satisfies such a need by providing a medicated patch that is effective, easy to apply, remains affixed for a useful period of time, and is reasonable in cost for the consumer. Such medicated patches are conveniently packaged separately and eliminate the immediate pain that occurs when a person is stung by a bee or wasp. The medicated patches also reduce the swelling associated with stings of that nature. Advantageously, the medicated patch for treating bee and wasp stings is produced in variety of different skin tone colors, such that no one has to feel self-conscious when wearing the medicated patch.

BRIEF SUMMARY OF THE INVENTION

In view of the foregoing background, it is therefore an object of the present invention to provide a medicated patch for treating bee and wasp stings. These and other objects, features, and advantages of the invention are provided by a medicated patch used to extract toxins from a human body surface.

The medicated patch includes a substrate layer formed from flexible material and has a substantially planar adhesive surface. Such a substrate layer has an annular shape and the adhesive surface spans along an entire top surface of the substrate layer.

A receptacle that has an annular shape is centrally registered on the adhesive surface in such a manner that the receptacle becomes permanently affixed to the substrate layer. Such a receptacle has an outer perimeter equidistantly spaced inwardly from an outer perimeter of the substrate layer such that a continuous band of the adhesive surface stretches beyond the outer perimeter of the receptacle.

A poultice is nested on the receptacle and confronts the outer perimeter of the receptacle. Such a poultice protrudes upwardly and away from the substrate layer such that the poultice becomes effectively intercalated between the human body surface and the substrate layer when a user affixes the medicated patch onto the human body surface. The poultice is housed in an inactive and dry state during pre-application conditions. Such a poultice is adaptable to an active and hydrated state during application procedures such that the poultice can advantageously effectively extract toxins from the human body surface. The poultice serves as a catalyst to the extraction process by drawing the toxins to it as a natural human body temperature thermally warms the poultice. With the poultice and body heat working together, the bee/wasp sting entry point remains open and exposed to the poultice wherein the toxins flow outwardly from the softened skin tissue in a natural and osmotic manner to the poultice.

The poultice preferably includes a predetermined quantity of tobacco covering a top surface area of the receptacle and a water pellet situated on top of the tobacco in such a manner that the water pellet is effectively prevented from hydrating the tobacco until a compressive force is applied to the water pellet for discharging and impregnating the tobacco with water. Such a water pellet has a spherical shape and is centrally registered with the outer perimeter of the receptacle.

The medicated patch may further include a package sized and shaped for conveniently housing the medicated patch therein. Such a package is formed from fluid-impermeable material readily compressible during the application procedures such that the poultice can advantageously be effectively hydrated without discharging undesired quantities of fluid from the package.

The package preferably has monolithically formed outer edge portions removably separable from a central region of the package such that the user can conveniently readily withdraw the medicated patch from the package without disturbing the active and hydrated state of the poultice. Such a package preferably further includes a top surface provided with surface indicia simulating a target zone for advantageously assisting the user to locate the water pellet during activating procedures.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 3:
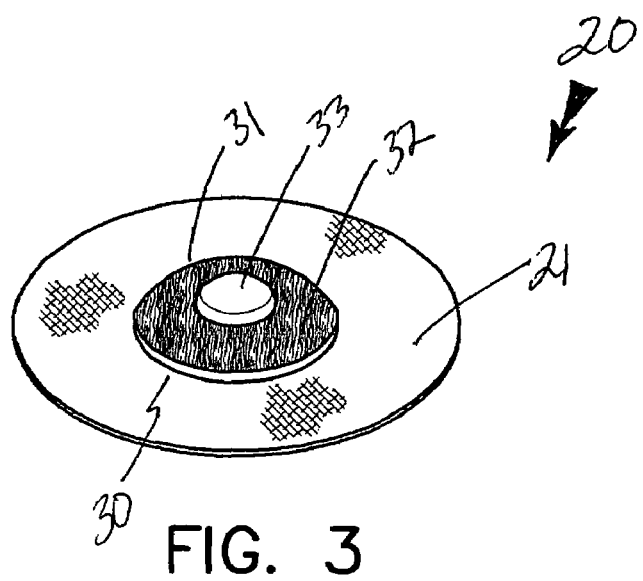
FIG. 3 is a perspective view of the medicated patch shown in FIG. 2 without the package.

Referring initially to FIG. 3, the medicated patch 10 includes a substrate layer 20 formed from flexible material and has a substantially planar adhesive surface 21. The adhesive layer 21 advantageously ensures that the medicated patch 10 remains in position for a sufficient amount of time in order for the medication to work properly. The substrate layer 20 has an annular shape and the adhesive surface 21 spans along an entire top surface of the substrate layer 20.

Figure 2:
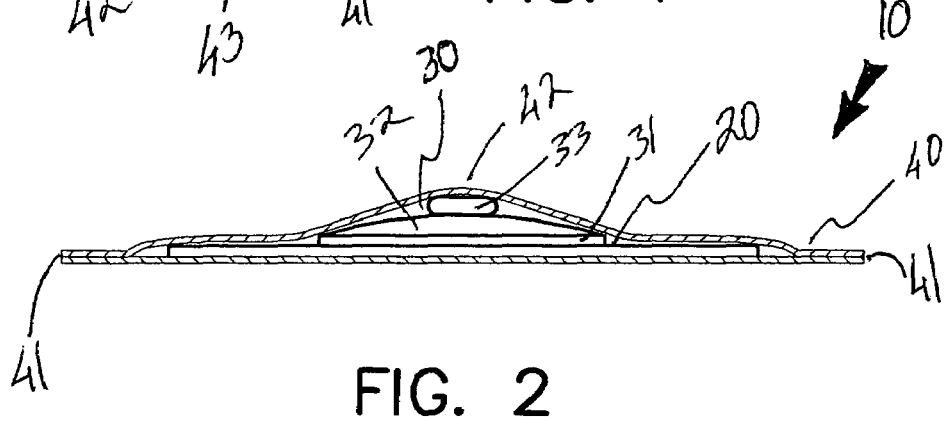
FIG. 2 is a cross-sectional view of the packaged medicated patch shown in FIG. 1.

Referring to FIGS. 2 and 3, a receptacle 30 that has an annular shape is centrally registered on the adhesive surface 21 in such a manner that the receptacle 30 becomes permanently affixed to the substrate layer 21. Such a receptacle 30 has an outer perimeter equidistantly spaced inwardly from an outer perimeter of the substrate layer 20 such that a continuous band of the adhesive surface 21 stretches beyond the outer perimeter of the receptacle 30.

Still referring to FIGS. 2 and 3, a poultice 31 is nested on the receptacle 30 and confronts the outer perimeter of the receptacle 30. Such a poultice 31 protrudes upwardly and away from the substrate layer 20 such that the poultice 31 becomes effectively intercalated between the human body surface and the substrate layer 20 when a user affixes the medicated patch 10 onto the human body surface. The poultice 31 is housed in an inactive and dry state during pre-application conditions, thus preventing same from losing its effectiveness, as is often the case when a poultice 31 is housed in a hydrated and active state. Such a poultice 31 is adaptable to an active and hydrated state during application procedures such that the poultice 31 can advantageously effectively extract toxins from the human body surface.

Again referring to FIGS. 2 and 3, the poultice 31 includes a predetermined quantity of tobacco 32 covering a top surface area of the receptacle 30 and a water pellet 33 situated on top of the tobacco 32 in such a manner that the water pellet 33 is effectively prevented from hydrating the tobacco 32 until a compressive force is applied to the water pellet 33 for discharging and impregnating the tobacco 32 with water. Of course, the poultice 31 may consist of alternate dehydrated medications, such as flax seed, Epsom salt, or fat back, for example, and the water pellet 33 may consist of sterile fluids other than water, or a combination of water and other sterile fluids, to hydrate such medications, as is obvious to a person of ordinary skill in the art. Such a water pellet 33 has a spherical shape and is centrally registered with the outer perimeter of the receptacle 30.

Figure 1:
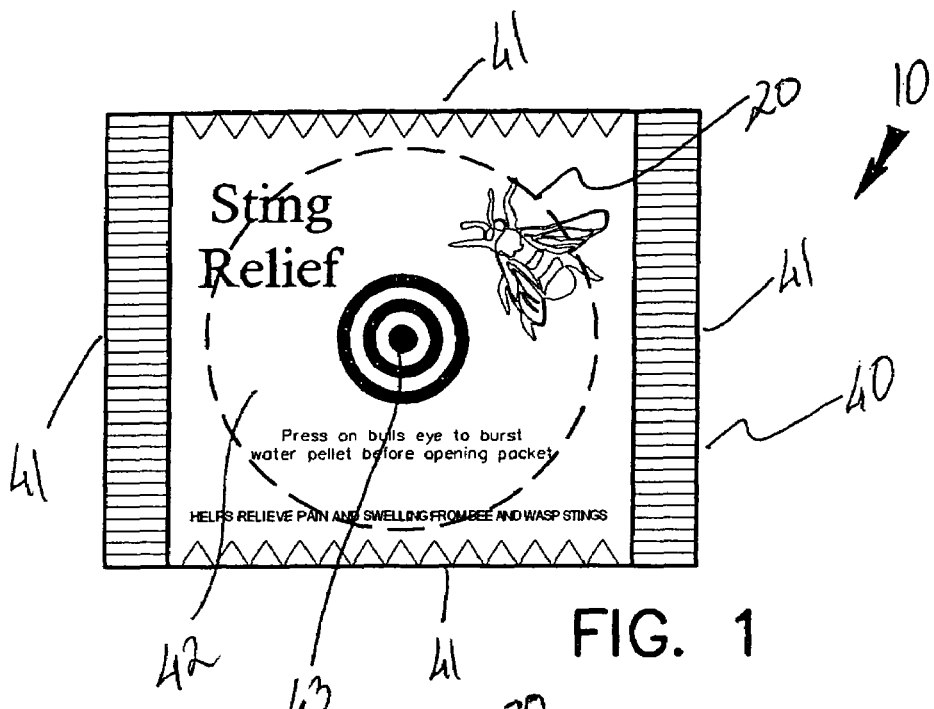
FIG. 1 is a top plan view showing a packaged medicated patch for treating bee and wasp stings, in accordance with the present invention.

Referring to FIGS. 1 and 2, the medicated patch 10 further includes a package 40 sized and shaped for conveniently housing the medicated patch 10 therein. Such a package 40 is formed from fluid-impermeable material readily compressible during the application procedures such that the poultice 31 can advantageously be effectively hydrated without discharging undesired quantities of fluid from the package.

Still referring to FIGS. 1 and 2, the package 40 has monolithically formed outer edge portions 41 removably separable from a central region of the package 40 such that the user can conveniently readily withdraw the medicated patch 10 from the package 40 without disturbing the active and hydrated state of the poultice 31. Such a package 40 further includes a top surface 42 provided with surface indicia 43 simulating a target zone for advantageously assisting the user to locate the water pellet 33 during activating procedures, thus assisting the user to position the poultice 31 over the stung area for optimal application of the medication. Of course, the medicated patch 10 may also be used to provide comfort to users suffering from anaphylactic shock, and would be applied in the same manner. The surface indicia 43 may be produced to simulate any number of objects or designs, as is obvious to a person of ordinary skill in the art.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A medicated patch used to extract toxins from a human body surface, said medicated patch comprising:

a substrate layer formed from flexible material and having a substantially planar adhesive surface, said adhesive surface spanning along an entire top surface of said substrate layer;

a receptacle centrally registered on said adhesive surface in such a manner that said receptacle becomes permanently affixed to said substrate layer, said receptacle having an outer perimeter equidistantly spaced inwardly from an outer perimeter of said substrate layer such that a continuous band of said adhesive surface stretches beyond said outer perimeter of said receptacle; and a poultice nested on said receptacle and confronting said outer perimeter of said receptacle, said poultice protruding upwardly and away from said substrate layer such that said poultice becomes intercalated between the human body surface and said substrate layer when a user affixes said medicated patch onto the human body surface, said poultice comprising a predetermined quantity of Nicotiana (tobacco) covering a top surface area of said receptacle and a water pellet situated on top of said Nicotiana (tobacco) in such a manner that said water pellet is prevented from hydrating said Nicotiana (tobacco) until a compressive force is applied to said water pellet for discharging and impregnating said Nicotiana (tobacco) with water;

wherein said poultice is housed in an inactive and dry state during pre-application conditions, said poultice being adaptable to an active and hydrated state during application procedures such that said poultice can effectively extract toxins from the human body surface.

2. The medicated patch of claim 1, wherein said water pellet has a spherical shape and is centrally registered with said outer perimeter of said receptacle.

3. In combination, the medicated patch of claim 1, and a package sized and shaped for housing said medicated patch therein, said package being formed from fluid-impermeable material readily compressible during the application procedures such that said poultice can be effectively hydrated without discharging undesired quantities of fluid from said package.

4. The combination of claim 3, wherein said package has monolithically formed outer edge portions removably separable from a central region of said package such that the user can readily withdraw said medicated patch from said package without disturbing the active and hydrated state of said poultice.

5. The combination of claim 3, wherein said package includes a top surface provided with surface indicia simulating a target zone for assisting the user to locate said water pellet during activating procedures.

6. A medicated patch used to extract toxins from a human body surface, said medicated patch comprising:

a substrate layer formed from flexible material and having a substantially planar adhesive surface, said substrate layer having an annular shape, said adhesive surface spanning along an entire top surface of said substrate layer;

a receptacle centrally registered on said adhesive surface in such a manner that said receptacle becomes permanently affixed to said substrate layer, said receptacle having an outer perimeter equidistantly spaced inwardly from an outer perimeter of said substrate layer such that a continuous band of said adhesive surface stretches beyond said outer perimeter of said receptacle; and a poultice nested on said receptacle and confronting said outer perimeter of said receptacle, said poultice protruding upwardly and away from said substrate layer such that said poultice becomes intercalated between the human body surface and said substrate layer when a user affixes said medicated patch onto the human body surface, said poultice comprising a predetermined quantity of Nicotiana (tobacco) covering a top surface area of said receptacle and a water pellet situated on top of said Nicotiana (tobacco) in such a manner that said water pellet is prevented from hydrating said Nicotiana (tobacco) until a compressive force is applied to said water pellet for discharging and impregnating said Nicotiana (tobacco) with water;

wherein said poultice is housed in an inactive and dry state during pre-application conditions, said poultice being adaptable to an active and hydrated state during application procedures such that said poultice can effectively extract toxins from the human body surface.

7. The medicated patch of claim 6, wherein said water pellet has a spherical shape and is centrally registered with said outer perimeter of said receptacle.

8. In combination, the medicated patch of claim 6 and a package sized and shaped for housing said medicated patch therein, said package being formed from fluid-impermeable material readily compressible during the application procedures such that said poultice can be effectively hydrated without discharging undesired quantities of fluid from said package.

9. The combination of claim 8, wherein said package has monolithically formed outer edge portions removably separable from a central region of said package such that the user can readily withdraw said medicated patch from said package without disturbing the active and hydrated state of said poultice.

10. The combination of claim 8, wherein said package includes a top surface provided with surface indicia simulating a target zone for assisting the user to locate said water pellet during activating procedures.

11. A medicated patch used to extract toxins from a human body surface, said medicated patch comprising:

a substrate layer formed from flexible material and having a substantially planar adhesive surface, said substrate layer having an annular shape, said adhesive surface spanning along an entire top surface of said substrate layer;

a receptacle having an annular shape and being centrally registered on said adhesive surface in such a manner that said receptacle becomes permanently affixed to said substrate layer, said receptacle having an outer perimeter equidistantly spaced inwardly from an outer perimeter of said substrate layer such that a continuous band of said adhesive surface stretches beyond said outer perimeter of said receptacle; and a poultice nested on said receptacle and confronting said outer perimeter of said receptacle, said poultice protruding upwardly and away from said substrate layer such that said poultice becomes intercalated between the human body surface and said substrate layer when a user affixes said medicated patch onto the human body surface, said poultice comprising a predetermined quantity of Nicotiana (tobacco) covering a top surface area of said receptacle and a water pellet situated on top of said Nicotiana (tobacco) in such a manner that said water pellet is prevented from hydrating said Nicotiana (tobacco) until a compressive force is applied to said water pellet for discharging and impregnating said tobacco with water;

wherein said poultice is housed in an inactive and dry state during pre-application conditions, said poultice being adaptable to an active and hydrated state during application procedures such that said poultice can effectively extract toxins from the human body surface.

12. The medicated patch of claim 11, wherein said water pellet has a spherical shape and is centrally registered with said outer perimeter of said receptacle.

13. In combination, the medicated patch of claim 11 and a package sized and shaped for housing said medicated patch therein, said package being formed from fluid-impermeable material readily compressible during the application procedures such that said poultice can be effectively hydrated without discharging undesired quantities of fluid from said package.

14. The combination of claim 13, wherein said package has monolithically formed outer edge portions removably separable from a central region of said package such that the user can readily withdraw said medicated patch from said package without disturbing the active and hydrated state of said poultice.

15. The combination of claim 13, wherein said package includes a top surface provided with surface indicia simulating a target zone for assisting the user to locate said water pellet during activating procedures.

* * * * *